(12) United States Patent
Southard et al.

(10) Patent No.: US 6,809,079 B2
(45) Date of Patent: Oct. 26, 2004

(54) COMPOSITIONS AND METHODS FOR TREATING FEMALE SEXUAL AROUSAL DISORDER USING HYDROPHOBIC-CALCITONIN GENE RELATED PEPTIDE

(75) Inventors: Jeffrey L. Southard, Olathe, KS (US); Gerald L. Yewey, Overland Park, KS (US); Gary J. Rosenthal, Louisville, CO (US)

(73) Assignee: VasoGenix Pharmaceuticals, Inc., Lenexa, KS (US)

( * ) Notice: Subject to any disclaimer, the term of this patent is extended or adjusted under 35 U.S.C. 154(b) by 97 days.

(21) Appl. No.: 10/041,244

(22) Filed: Jan. 8, 2002

(65) Prior Publication Data

US 2003/0130183 A1 Jul. 10, 2003

(51) Int. Cl.$^7$ .............................................. A61K 38/00
(52) U.S. Cl. ....................... 514/12; 424/725; 424/737; 424/739
(58) Field of Search ............................ 514/2; 424/725; 424/737, 739

(56) References Cited

U.S. PATENT DOCUMENTS

| | | | |
|---|---|---|---|
| 5,214,030 A | | 5/1993 | Stief |
| 5,576,290 A | * | 11/1996 | Hadley .......................... 514/11 |
| 5,958,877 A | * | 9/1999 | Wimsalawansa ............. 514/12 |
| 6,051,555 A | * | 4/2000 | Hadley .......................... 514/11 |

OTHER PUBLICATIONS

Aquaphor. http://www.dermstore.com/product_Original+ Ointment_433.htm.*
International Search Report, PCT/US02/24974.
Brian B. Quebbeman, et al. "Effect of calcitonin gene–related peptide on well–developed canine coronary collateral vasculature," *J. Cardiovascular Pharm.*, 21 (1993) 774–780.
Peter R. Ludman, et al., "Effects of calcitonin gene–related peptide on normal and atheromatous vessels and on resistance vessels in the coronary circulation in humans," *Circulation*, 84:5 (Nov. 1991) 1993–2000.
Jacek J. Prieblsz, "Calcitonin gene–related peptide and regulation of human cardiovascular homeostasis," *American J. of Hypertension*, 6:5 (May 1993) 434–450.
Neal G. Uren, et al., Effect of intravenous calcitonin gene–related peptide on ischaemia threshold and coronary stenosis saverity in humans, *Cardiovascular Res.*, 27 (1993) 1477–1481.
Donald J. DePette and Sunll Wimalawansa, "Cardiovascular actions of calcitonin gene–related peptide," *Calcium Regulating Hormones and Cardiovascular Function*, (1994) 239–252.
Nobuyo Sekiguchi, et al., "Effect of calcitonin gene–related peptide on coronary microvessels and its role in acute myocardial ischemia," *Circulation* 89:1 (Jan. 1994) 366–374.

Sunil Wimalawansa, "Calcitonin: Molecular biology, physiology, pathophysiology and its therapeutic uses," 121–160, not dated.
Sunil Wimalawansa, "Isolation, purification, and biochemical characterisation of calcitonin gene–related peptide receptors," *Annals New York Academy of Science*, 657 (1992) 70–87.
"Medical Management of Erectile Dysfunction: A Primary–Care Manual", Harin Padma–Nathan, MD, Professional Communications, Inc., Ed., First edition, Copyright 1999.
"Erectile Dysfunction: A Clinical Guide", Roger Kirby, et al., Isis Medical Media Ltd., Ed., 1999.
Jean McEwan, et al. "Calcitonin gene–related peptide: a potent dilator of human epicardial coronary arteries," *Circulation*, 74:6 (Dec. 1986) 1243–1247.
Michael G. Rosenfeld, et al. "Production of a novel neuropeptide encoded by the calcitonin gene via tissue–specific RNA processing," *Nature*, 304:14 (Jul. 1983) 129–135.
Howard R. Morris, et al. "Isolation and characterization of human calcitonin gene–related peptide," *Nature*, 308:19 (Apr. 1984) 746–748.
P.H. Steenberg, et al. "A second human calcitonin/CGRP gene," *FEBS* 183:2 (Apr. 1985) 403–407.
J.W.M. Hoppener, et al. "The second human calcitonin/CGRP gene is located on chromosome 11, " *Human Genetics* 70 (1985) 259–263.
David Ezra, et al. "Calcitonin gene–related peptide: a potent modulator of coronary flow," *European J. of Pharm.*, 137 (1987) 101–105.
T. Shoji, et al., "Vasodilating effects of human and rat calcitonin gene–related peptides in isolated porcine coronary arteries," *Naunyn–Schmiedeberg's Arch Pharmacol.*, 336 (1987) 438–444.
J.R. McEwan, et al. "Vasodilatation by calcitonin gene–related peptide and by substance P: a comparison of their effects on resistance and capacitance vessels of human forearms," *Circulation*, 77:5 (May 1988) 1072–1080.
Sunil J. Wimalawansa, et al., "Isolation, purification and characterization of beta–hCGRP from human spinal cord, " *Biochem. and Biophys. Res. Comm.*, 167:3 (Mar. 1990) 993–1000.
Sunil J. Wimalawansa, "Use of synthetic peptides in specific affinity chromatography for purification of specific peptide receptors," *Innovation and Perspectives in Solid Phase Synthesis: (Peptides, Polypeptides and Oliconucleotides)*, (1992) 111–119.

\* cited by examiner

*Primary Examiner*—Christopher R. Tate
*Assistant Examiner*—Maury Audet
(74) *Attorney, Agent, or Firm*—Morrison & Foerster LLP

(57) ABSTRACT

The present invention provides a method and composition for the treatment of Female Sexual Arousal Disorder. Calcitonin gene-related peptide, a naturally occurring substance in the human body, is chemically conjugated to a hydrophobic agent thereby increasing its permeability across the skin membrane. When locally applied to female genitalia localized blood flow is promoted thus resulting in increased sexual arousal.

16 Claims, No Drawings

COMPOSITIONS AND METHODS FOR TREATING FEMALE SEXUAL AROUSAL DISORDER USING HYDROPHOBIC-CALCITONIN GENE RELATED PEPTIDE

BACKGROUND OF THE INVENTION

1. Field of the Invention

The present invention relates to compositions and methods for the local administration of a therapeutic preparation for treating female sexual arousal dysfunction, and more particularly, to a preparation comprising calcitonin gene-related peptide conjugated to a hydrophobic agent and methods of use for promoting blood flow to the genital region, specifically the clitoris of a female patient.

2. Description of the State of Art

According to the Journal of the American Medical Association, more than 43% of American women (about 40 million) experience some form of sexual disorder. Other reports state that 70% of post-menopausal and 25% of pre-menopausal women experience sexual dysfunction. Any woman can experience Female Sexual Dysfunction at some point in her life. Physicians and other healthcare providers recognize Female Sexual Dysfunction as a medical condition. It includes a variety of disorders that are related to the desire for sex, arousal during sexual activity, problems with orgasm or pain during sexual activity. If a woman's sexual concerns are recurring in nature and cause her personal distress, she may indeed have female sexual dysfunction.

Specifically, Female Sexual Dysfunction is divided into categories related to desire, orgasm, arousal and pain.

Disorders of Sexual Arousal

It is believed that the difficulty or inability to achieve clitoral tumescence may be related to and associated with other symptoms of female sexual arousal disorder. According to the International Consensus Report on Female Sexual Dysfunction, Female Sexual Arousal Disorder (FSAD) is defined as the persistent or recurrent inability to attain or maintain adequate genital lubrication or swelling responses. FSAD may be expressed as a lack of subjective excitement or lack of genital (lubrication/swelling) or other somatic responses (AFUD Consensus Report of FSD, 1998). Reduced sexual arousal may result in discomfort or even pain due to insufficient vaginal lubrication and/or a lack of physical preparation of the genitalia for sexual activity. Although female sexual arousal disorder is often a change from a previous state of arousability, in some cases it is a lifelong condition.

The clitoris in the human female consists of a cylindrical, erectile organ composed of three parts: The outermost glans or head, the middle corpus or body, and the innermost crura. The glans of the clitoris is visualized as it emerges from the labia minora, which bifurcates to form the upper prepuce anteriorly and the lower frenulum posteriorly. The body of the clitoris consists of two paired corpora cavernosa of about 2.5 cm in length. The body extends under the skin at the corona to the crura. The two crura of the clitoris, formed from the separation of the most proximal portions of the corpora in the perineum, attach bilaterally to the undersurface of the symphysis pubis at the ischiopubic rami.

A fibrous tunica albuginea enseathes each corporal body made up of lacunar space sinusoids surrounded by trabecula of the vascular smooth muscle and collagen connective tissue. No retractor clitoridis muscle exists in humans as it does in other animals such as cattle and sheep, however a supporting suspensory ligament does hold the clitoris in the introital region.

The main arterial supply to the clitoris is from the ilio-hypogastric-pudendal arterial bed. The internal pudendal artery is the last anterior branch off the internal iliac artery. Distally, the internal pudendal artery traverses Alcock's canal, then terminates as it supplies the inferior rectal and perineal artery which supply the labia. The common clitoral artery continues to the clitoris. This artery bifurcates into a dorsal clitoral artery and a cavernosal clitoral artery.

In the normal female, autonomic efferent innervation of the clitoris passes from the pelvic and hypogastric nerves to the clitoris. Pelvic nerve stimulation results in clitoral smooth muscle relaxation in an increase in clitoral cavernosal artery inflow and an increase in clitoral intracavernous pressure, which lead to tumescence and extrusion of the glans clitoris.

Clitoral erectile insufficiency or reduced clitoral arterial flow may be caused by cardiac insufficiency, atherosclerosis, medication, diabetes mellitus, smoking, certain sexually transmitted diseases, nerve damage may have a negative effect on physiological, or age-related causes, among other factors. Women who are breastfeeding often report a reduction in vaginal lubrication. Reduced levels of estrogen during and after menopause also contributes to arousal difficulties as well.

Reduced clitoral arterial flow may lead to fibrosis of the clitoral cavernosa and reduced clitoral physiological function. In an animal model, Park, et al., demonstrated that significant collagen build up occurs when the arterial inflow to the clitoris is compromised. This work demonstrated the importance of maintaining arterial flow to the clitoris to prevent collagen build up and fibrosis of the smooth muscle. See Park, K., et al., "Vasculogenic Female Sexual Dysfunction: The Hemodynamic Basis for Vaginal Engorgement Insufficiency and Clitoral Erectile Insufficiency," *IJIR*, 9:27–37 (1997).

Certain medication can also interfere with arousal. Antidepressants, antihypertensives, and antihistamine medications are commonly associated with adverse sexual side effects. The direct physiological effects of these drugs interfere with the processes involved in sexual excitement.

Treatments to Enhance Sexual Arousal in Women

Most of the treatments for sexual arousal disorders are still in the experimental stages, although a variety of products are being evaluated for their effectiveness in increasing blood flow to the genitalia and facilitating lubrication. Several vasodilator creams are being tested to measure their ability to improve sexual arousal. These creams work by expanding the arteries to increase blood flow to genital tissue. A number of oral medications are being investigated as well, including Viagra and related drugs, "natural" supplements such as DHEA and yohimbine, dopamine agonists, and drugs that stimulate the sympathetic nervous system. These drugs work by promoting blood flow, stimulating certain components of the nervous system, or a combination of both. Because most of these studies are fairly recent (or ongoing), there is not yet an FDA-approved medication for female sexual arousal disorder.

The FDA recently approved a new non-pharmaceutical product to aid sexual arousal in women. EROS-CVD is a small device that creates a gentle suction over the clitoris in order to increase blood flow and sensation. It is available only by prescription.

Until recently, most vasculogenic sexual-dysfunction research has focussed on males, e.g., on physiologic causes of erectile insufficiency. Abnormal reduction of blood flow through the penile cavernosal arteries and excess venous outflow, i.e., veno-occlusive dysfunction, are well-recognized physiologic causes of impotence and have been the subject of intense study. Now, however, an increasing amount of research is being conducted in the field of vasculogenic female sexual dysfunction.

Studies of sexual dysfunction in couples have revealed that more females than males may experience arousal or orgasmic problems. Whereas 40% of men experienced erectile or ejaculatory dysfunction in one such study, arousal or orgasmic dysfunctions affected 63% of women. See Frank, E., et al., "Frequency of sexual dysfunction in 'normal' couples," N. Engl. J. Med., 299:111–115 (1978), which is incorporated herein by reference. Vasculogenic factors are thought to be one of the primary causes of female sexual dysfunction, and increasing age and the onset of menopause contribute to the problem.

It is known that during normal sexual function, the female undergoes many physiological changes. These changes include, among others, increased labial flow, dilation of the introitus, changes in vaginal-wall blood flow (resulting in color change, for example), vaginal lubrication (transudates), vaginal dilation, vaginal lengthening, nipple and clitoral erections, muscle contractions, pupil dilation, increased blood pressure and heart rate, and skin blushing.

Because the prior art has focused primarily on erectile insufficiency in males and other male-related problems, there have been relatively few attempts to effectively determine and treat causes of female sexual dysfunction, for example by monitoring or measuring the above-referenced physiological changes that the female under goes during sexual arousal.

There is still a need, therefore, for a non-oral composition that when applied to the female genitalia and specifically the clitoris will result in the ability to achieve clitoral tumescence.

SUMMARY OF THE INVENTION

Accordingly, one object of this invention is to provide a method and composition for treating Female Sexual Arousal Disorder.

Another object of this invention is to provide a composition that when applied to the clitoris results in clitoral tumescence.

Additional objects, advantages, and novel features of this invention shall be set forth in part in the description and examples that follow, and in part will become apparent to those skilled in the art upon examination of the following or may be learned by the practice of the invention. The objects and the advantages of the invention may be realized and attained by means of the instrumentalities and in combinations particularly pointed out in the appended claims.

DETAILED DESCRIPTION OF THE PREFERRED EMBODIMENT

The present invention provides a method and composition for the treatment of female sexual arousal disorder (FSAD) using calcitonin gene-related peptide (CGRP) conjugated to a hydrophobic agent, hereinafter referred to as hydrophobic-CGRP. CGRP is a naturally occurring vasodilator substance in the human body. As such, CGRP does not have the same toxicity and allergy problems as the foreign substances that currently are used for similar purposes. When locally applied or infused, the effects of CGRP are limited to a local vascular area. Virtually no systemic effects are induced, making CGRP extremely safe and effective.

CGRP is a 37-amino acid neuropeptide, which is the most potent naturally occurring vasodilator peptide in the human body. CGRP is distributed throughout the central and peripheral nervous systems, and is found in areas that are known to be involved in cardiovascular function. Peripherally, CGRP is found in the heart, particularly in association with the sinoatrial and atrioventricular nodes. In addition, CGRP is found in nerve fibers that form a dense periadventitial network throughout the peripheral vascular system, including the cerebral, coronary, and renal arteries. CGRP has prominent cardiovascular effects, including vasodilation and positive chronotropic and inotropic effects, which may play an important role in normal cardiovascular function.

CGRP occurs in two known forms in the human body, an α- and a β-form. The α- and β-strains of CGRP both are present in plasma, cerebrospinal fluid, and the spinal cord. See, Wimalawansa, S. J., Morris, H. R., MacIntyre, I. J., Mol. Endocrinol., 3:247 (1989), incorporated herein by reference. Both forms have been isolated and fully characterized by amino acid sequencing and fast atom bombardment-mass spectrometry (FABMS). Wimalawansa, S. J., Morris, H. R., Etienne, A., Blench, I., Panico, M., and MacIntyre, I., "Isolation, purification and characterization of β-hCGRP from human spinal cord," Biochem. Biophys. Res. Commun., 167: 993 (1990); Steenberg, et al. FEBS Letts., 183:403 (1985); incorporated herein by reference. Genes for CGRP have been identified on chromosome 11. Hoopener, et al., Hum. Gen., 70:259 (1985). CGRP receptors have been isolated and purified, and monoclonal antibodies have been raised against these purified receptors. Wimalawansa, S. J., "Isolation and characterization of calcitonin gene-related peptide receptors and raising monoclonal antibodies," Annals of New York Academy of Sciences, 657:70–87 (1992); Wimalawansa, S. J., Gunasekera, R. D., Zhang, F., "Isolation, purification, and characterization of calcitonin gene-related peptide receptor," Peptides, 14:691–699 (1993); and Proceedings, First International Symposium on Calcitonin Gene-Related Peptide," Graz., Austria, Regul., Peptides, 14:691 (1993).

The preferred form of CGRP for use in the present invention begins with CGRP that is synthesized using an automatic peptide synthesizer using well known methods. The amino acid sequence of the α- and β-forms of CGRP are known and differ in structure by only three amino acids. Each possesses equal biological activity in the cardiovascular system. Once the desired CGRP is obtained chemical conjugation to a hydrophobic agent may proceed thereby forming the desired hydrophobic-CGRP for use in the present invention.

A preferred method for synthesizing the CGRP is the well known Merrifield method. Merrifield, R. B., J. Am. Chem. Soc., 85:2149 (1963); Merrifield, R. B., Science, 232:341 (1986), both incorporated herein by reference. See also Wimalawansa, S. J., "Use of synthetic peptides in specific affinity chromatography for purification of specific peptide receptors," Innovation and Perspectives in Solid Phase Synthesis (Peptides, Polypeptides and Oligonucleotides), (Ed.) R. Epton, Intercept Ltd., Andover, UK (1991) 111–119, incorporated herein by reference. Either t-Boc, F-Moc, or fast-Moc solid-phase peptide chemistry may be used to synthesize the peptide.

Once synthesized, the authenticity of the resulting peptide may be verified using known procedures, such as fast atom bombardment mass spectroscopy, amino acid sequencing and analysis. After synthesis, the peptide preferably should be filter sterilized (0.2 μm), aliquoted, lyophilized, and stored in sterile ampoules or in catheters. Just prior to conjugation to a hydrophobic agent, the lyophilized powder should be dissolved in sterile normal saline (0.9% NaCl in water).

Human CGRP also may be obtained commercially, e.g., from: Peninsula Laboratory, located in Belmont, Calif.; Bachem Biosciences, Inc., located in King of Prussia, Pa.; and Sigma Chemicals, located in St. Louis, Mo. Commercial grade human CGRP is not marketed for human use; therefore, commercially available human CGRP's may be used in the present invention only if they are purified and sterilized so that they are fit for human use. Genetically engineered human CGRP also may be used in the present invention. Similar results also could be achieved using a CGRP analogue or an analogue based on the CGRP "receptor structure." These include peptide-based analogues, as well as peptide-mimetic analogues. Animal-derived CGRP's are biologically active and thus could be used in the present invention; however, as a practical matter, animal-derived CGRP's present allergy and autoimmune problems which preferably should be avoided.

In a preferred embodiment, the CGRP is conjugated to linolenic acid, a naturally occurring polyunsaturated fatty acid, as an ester. (Acetoxymethyl acetate or acetoxymethyl esters can also be used for this purpose instead of linolenic acid.) This CGRP ester (conjugate) may be prepared using an automated peptide synthesizer and known methods. Alternately, the CGRP ester may be prepared by reacting the CGRP and linolenic acid using carbodiimide, glutaraldehyde, or a similar compounds, as a coupling agent.

In the case of conjugation of CGRP to a fatty acid manually, a 1:1 weight ratio of CGRP should be allowed to react with citraconic anhydride at a pH of 8.5 (to block free amine groups) while mixing with a magnetic stir bar. After 60 minutes at room temperature, the blocked peptide should be separated from other free compounds by a G10 gel-permeation column. The blocked peptide then should be allowed to react with the same weight of coupling reagent and the pH should be adjusted to 8.0. The mixture should be incubated for 10 minutes and an equal volume of fatty acid—preferably linolenic acid, $C_{18}H_{30}O_2$ (FE 278.4). In molar proportions, about 50 mol of fatty acid should be added for every 1 mol of peptide. After four hours at room temperature, 100 mmol/L of sodium acetate (pH 4.2) should be added to terminate the reaction. The resultant material should be dialyzed to remove the sodium acetate with 5 changes of buffer. The material then should be dialyzed overnight against phosphate buffered saline (pH 7.4) to remove all uncoupled reagents. This last dialysis step (i.e., separation of the conjugated compound) also may be achieved by gel-permeation chromatography.

Alternatively, hydrophobic-CGRP may be prepared by linking the N-terminal amino group of CGRP to the C-terminal carboxyl group via (acyloxy) alkoxy promoiety Boc. In this convergent approach, this pro-peptide is reacted with 1-chloromethyl chloroformate with p-nitrophenol in the presence of N-methylmorpholine (NMM) to afford 1-Chloromethyl)-p-nitrophenyl carbonate. Substitution of the chloride can be achieved with iodide, leading to iodo compounds with high yield. The resultant compound is then reacted with the cesium salt of Boc-Ala in dimethyl-formamide (DMF) to give a mixture of the desired product Boc-(alaninyloxy) methyl p-nitrophenyl carbonate, and the side product of p-nitrophenyl ester of Boc-alanine (Boc-Ala-OpNP). This mixture then couples with Trp-Obzl in the presence of NMM and 1-hydroxybenzotri-azole (HOBT) in hexamethylphos-phoramide (HMPA) to afford the Boc-[[(alaninyloxy)methyl]-carbonyl]-N-tryptophan benzyl ester and the side product of Boc-Ala-Trp-OBzl. Hydrogenolysis of this mixture using 10% Pd/C as catalyst under the $H_2$ atmosphere in EtOH will give over 95% pure compound of interest. The active compound is then purified from the side product Boc-Ala-Trp-OH by reverse-phased high performance liquid chromatography. In vivo, this cyclic pro-peptide will release linear CGRP, which is biologically active.

Other embodiments contemplate the use of unconjugated CGRP in its natural form, fragments thereof or polypeptides containing the active sites of the CGRP protein or analogues thereof. Polypeptides and the sequences thereof may be determined as discussed by Wimalawansa, S. J., "Calcitonin Gene-related Peptide and Its Receptors: Molecular Genetics, Physiology, Pathology, and Therapeutic Potentials," *Endocrine Reviews*, 17(5):533–585 (1996), incorporated herein by reference.

Once the CGRP ester is formed, the CGRP ester should be mixed with a pharmaceutically acceptable base cream such as a lipophilic or aqueous based cream to result in a concentration of 2.5 nmol/dose (10.18 μg/dose). A preferred cream is a lipophilic base such as but not limited to Aquaphore™. Various additives included in the composition of the present invention include but are not limited to flavoring agents, vitamin E, L-Arginine, L-Valine, peppermint oil, ginger oil, cinnamon oil, *Gynostemma pentaphyllum, Crataegus pinnatifidia*, Yohimbine, prostaglandin $E_1$, ($PGE_1$). Other additives such as, but not limited to ethylene oxide and propylene oxide block copolymers (pluronics) that are widely known as agents that promote drug penetration across biological barriers can further be added. Pluronics L61 and P85 that have different hydrophobicity are examples of such block copolymers.

The compounds and/or compositions of the invention can be administered by any available and effective delivery systems including, but not limited to, by topical application to the clitoris, or transdermally, in dosage unit formulations containing conventional nontoxic pharmaceutically acceptable carriers, adjuvants, and vehicles, as desired. The route of administration is at the discretion of the physician who takes into consideration the condition of the patient undergoing treatment.

After topical application of about 0.1–0.5 ml of the CGRP cream and gentle rubbing, the "fatty acid-CGRP ester" will readily penetrate through the skin and accumulate in the cavernosa corpora. Naturally occurring esterases in the subcutaneous tissues will then release active CGRP into the local environment from the fatty acid conjugate. The result is rapid and sustained vasodilation of the blood vessels responsible for clitoral erection. The effect of the CGRP should last between about 20–45 minutes. The local application may be repeated, if necessary, to result in a continued state of arousal lasting about 20–45 minutes. Persons of skill in the art can adjust the foregoing parameters to locally apply CGRP to other sites in the body.

Formulations of hydrophobic-CGRP, CGRP or fragment thereof can conveniently be presented in unit dosage forms and can be prepared by any of the methods known in the pharmaceutical arts. Transdermal drug administration, which is known to one skilled in the art, involves the delivery of pharmaceutical agents via percutaneous passage of the drug into the systemic circulation of the patient.

Topical administration can also involve transdermal patches or iontophoresis devices. Other components can also be incorporated into the transdermal patches. For example, compositions and/or transdermal patches can be formulated with one or more preservatives or bacteriostatic agents including, for example, methyl hydroxybenzoate, propyl hydroxybenzoate, chlorocresol, benzalkonium chloride, and the like.

Dosage forms for topical administration of the compounds and/or compositions of the invention can include creams, sprays, lotions, gels, ointments, and the like. Administration of the cream or gel can be accompanied by use of an applicator or vaginal insert or device, and is within the skill of the art. Typically, any pharmaceutically acceptable preparation may be used, in particular a preferred cream being Aquaphore, which is commercially available from Beiersdorf Inc., Norwalk, Conn. The concentration of CGRP in the cream should range from about 1–3 nmol/dose (4.07–12.22 μg/dose), and in one preferred embodiment be about 2.5 nmol/dose (10.18 μg/dose). A lubricant can also be included in the formulation or provided for use as needed. Lubricants include, for example, K-Y jelly (available from Johnson & Johnson) or a lidocaine jelly, such as Xylocaine 2% jelly (available from Astra Pharmaceutical Products).

The compounds and/or compositions of the invention will typically be administered in a pharmaceutical composition containing one or more selected carriers or excipients. Suitable carriers include, for example, water, silicone, waxes, petroleum jelly, polyethylene glycol, propylene glycol, liposomes, transfersomes, vitamin E, sugars, and the like. The compositions can also include one or more permeation enhancers including, for example, vitamin E, L-Arginine, L-Valine, dimethylsulfoxide (DMSO), dimethyl formamide (DMF), N,N-dimethyl-acetamide (DMA), decyl-methylsulfoxide (C10MSO), polyethylene glycol monolaurate (PEGML), glyceral monolaurate, lecithin, 1-substituted azacycloheptan-2-ones, particularly 1-N-dodecylcyclazacylcoheptan-2-ones (available under the trademark Azone from Nelson Research & Development Co., Irvine, Calif.), alcohols and the like.

Suppositories for vaginal administration of the compounds and/or compositions of the invention can be prepared by mixing the drug with a suitable nonirritating excipient such as cocoa butter and polyethylene glycols which are solid at room temperature but liquid at vaginal temperature, such that they will melt in the vagina and release the drug.

"Therapeutically effective amount" refers to the amount of hydrophobic-CGRP and/or other vasoactive agents that are effective to achieve its intended purpose. While individual patient needs may vary, determination of optimal ranges for effective amounts of hydrophobic-CGRP and/or other vasoactive agents is within the skill of the art. Generally, the dosage required to provide an effective amount of the compound and/or composition, and which can be adjusted by one of ordinary skill in the art will vary, depending on the age, health, physical condition, weight, extent of the dysfunction of the recipient, frequency of treatment and the nature and scope of the dysfunction.

The amount of a given of hydrophobic-CGRP and/or other vasoactive agents of the present invention which will be effective in the treatment of a particular dysfunction or condition will depend on the nature of the dysfunction or condition, and can be determined by standard clinical techniques, including reference to Goodman and Gilman, The Pharmacological Basis of Therapeutics (9th Edition, 1995); The Physician's Desk Reference (49th Ed.); Medical Economics (1995); Drug Facts and Comparisons (1993); and The Merck Index (12th Ed.), Merck & Co., Inc. (1996), the disclosures of each of which are incorporated herein by reference in their entirety. The precise dose to be used in the formulation will also depend on the route of administration, and the seriousness of the dysfunction or disorder, and should be decided by the physician and the patient's circumstances.

It is contemplated that the usual dose of hydrophobic-CGRP and/or other vasoactive agents administered to a patient is about 1.0 μg/dose to about 100.0 μg/dose, preferably about 5.0 μg/dose to about 50 μg/dose, more preferably about 10.0 μg/dose. Effective doses can be extrapolated from dose-response curves derived from in vitro or animal model test systems and are in the same ranges or less than those described for other commercially available compounds in, for example, the Physician's Desk Reference (49th Ed.).

The dosage regimen for treating a condition with the compounds and/or compositions of the invention is selected in accordance with a variety of factors, including the type, age, weight, sex, diet and medical condition of the patient, the severity of the dysfunction, the route of administration, pharmacological considerations such as the activity, efficacy, pharmacokinetic and toxicology profiles of the particular compound used, whether a drug delivery system is used, and whether the compound is administered as part of a drug combination. Thus, the dosage regimen actually used can vary widely and therefore may deviate from the preferred dosage regimen set forth above. Additional doses may be applied as needed.

Particularly preferred methods of administering of hydrophobic-CGRP and/or other vasoactive agents for the treatment of female sexual dysfunctions are topical application, or transdermal application, by inhalation or by the use of suppositories.

The present invention also provides pharmaceutical kits comprising one or more containers filled with one or more of the ingredients of the pharmaceutical compounds and/or compositions of the present invention, including, one or more of hydrophobic-CGRP and/or other vasoactive. One embodiment would include a container having at least two distinct chambers, wherein one chamber would contain hydrophobic-CGRP and another chamber would contain the delivery vehicle, such that as the hydrophobic-CGRP and delivery vehicle are dispensed they are also mixed prior to application. Such kits can also include, for example, other compounds and/or compositions (e.g., permeation enhancers, lubricants), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

The invention is further illustrated by the following non-limited examples. All scientific and technical terms have the meanings as understood by one with ordinary skill in the art. The specific examples which follow illustrate the methods in which the hydrophobic-CGRP containing compositions of the present invention may be utilized and are not to be construed as limiting the invention in sphere or scope. The methods may be adapted to variation in order to produce compositions embraced by this invention but not specifically disclosed. Further, variations of the methods to produce the same compositions in somewhat different fashion will be evident to one skilled in the art.

EXAMPLES

The examples herein are meant to exemplify the various aspects of carrying out the invention and are not intended to limit the invention in any way.

Example 1

The hydrophobic-CGRP according to the present invention may be mixed with Aquaphore cream to result in a concentration of 2.5 nmol/dose (10.18 μg/dose. About 0.1 to 0.5 ml of the hydrophobic-CGRP cream would then be applied on the surface of the clitoris with gentle rubbing. This local application of hydrophobic-CGRP containing cream can be repeated as necessary.

Example 2

Topical Application of Hydrophobic CGRP to Decrease Refractory Time in Healthy Male Volunteers This was an unofficial study conducted by the inventors to demonstrate proof of concept in humans for the invention. The study designed was a single blind, placebo controlled, single-dose, single and multiple application study to evaluate the safety and efficacy of CGRP-linolenic acid conjugate (hydrophobic-CGRP) applied topically to induce erections in six healthy male volunteers. Formulation A consisted of hydrophobic-CGRP mixed with Aquaphore cream (petroleum jelly/water emulsion) to a concentration of 10.18 μg/mL, formulation B, the placebo, was the Aquaphore vehicle. Six subjects received both formulation A and formulation B, and were instructed to apply each formulation on successive days (i.e. formulation A on one day, and formulation B the next day), and to do this on 3 separate occasions (n=18 applications). For each application, the subjects applied 0.5–1.0 mL of the cream to the ventral surface of the penis, and gently worked the cream into the skin without any additional manipulation or the assistance of visual aids. The subjects were instructed to determine if an erection suitable for intercourse was induced, time to onset of erection, and duration of erection for each application and write down the outcome. Two subjects who obtained consistent erections with formulation A in the first study, were asked to reapply the cream, and then after the erection subsided to immediately apply the cream 2 more times immediately following an erection (n=6 applications). For single application subjects, erections were achieved in 15 of 18 applications (83%) of hydrophobic-CGRP vs. 3 of 18 applications (17%) for placebo. Average time of onset of was 10 minutes for both formulations, with the erections lasting 15–40 minutes (averaging 20 minutes) for hydrophobic-CGRP versus a few minutes for placebo. Suprisingly, two subjects who did multiple applications of the hydrophobic-CGRP, reported repeat erections suitable for intercourse in 5 of 6 applications (83%), with a time of onset of 10 minutes, and durations greater than 10 minutes, suggesting that there was no tachyphylaxis in response to multiple applications. No other known drug is capable of achieving this result. Furthermore, systemic adverse effects were observed, and no pain, burning, tingling or warm sensations were reported. The only adverse effects observed were mild, localized, transient flushing of the penile skin on all subjects when applying the hydrophobic-CGRP formulation.

This study demonstrates the safety and efficacy of single and multiple applications of a preliminary hydrophobic-CGRP formulation, topically and locally applied to induce erections in healthy males. Unlike most erectile dysfunction studies, this study did not use visual aids or additional manipulation to enhance the psychosexual-physiological response to induce sexual arousal. The results observed were due to the pharmacological effects of CGRP. Of note, it is significant that there was no tachyphylaxis, decrease in the drug response following repetitive application. Currently there are no products on the market or in development that permit unrestricted re-application due to formulation irritation, systemic side effects, and tachyphylaxis. An optimized formulation containing specific dermal penetration enhancers has the potential to increase efficacy, decrease the time of onset, and extend the duration of an erection, as well as permit re-application.

Example 3

Below are numerous exemplary preparations of the present invention as a weight to weight ratio. CGRP, CGRP analogues, and polypeptides containing the active site of CGRP can be substituted for hydrophobic-CGRP.

1. 0.001% hydrophobic-CGRP, 99.999% vitamin E.
2. 0.001% hydrophobic-CGRP, 99.999% cocoa butter.
3. 0.001% hydrophobic-CGRP, 99.999% glycerine.
4. 0.001% hydrophobic-CGRP, 99.999% carboxymethylcellulose.
5. 0.001% hydrophobic-CGRP, 99.999% hydroxymethylcellulose.
6. 0.001% hydrophobic-CGRP, 99.999% methylparaben.
7. 0.001% hydrophobic-CGRP, 99.999% propylene glycol.
8. 0.001% hydrophobic-CGRP, 99.999% polyethylene glycol.
9. 0.001% hydrophobic-CGRP, $\geq$9.999% vitamin E, $\leq$90% cocoa butter and/or DI water and/or polyglycerylmethacrylate and/or glycerine and/or carboxymethylcellulose and/or hydroxymethylcellulose and/or methylparaben and/or propylene glycol and/or polyethylene glycol and/or sodium benzoate.
10. 0.001% hydrophobic-CGRP, $\leq$1% cinnamon and/or ginger and/or peppermint oil, $\geq$9.990% vitamin E, $\leq$90% cocoa butter and/or DI water and/or polyglycerylmethacrylate and/or glycerine and/or carboxymethylcellulose and/or hydroxymethylcellulose and/or methylparaben and/or propylene glycol and/or polyethylene glycol and/or sodium benzoate.
11. 0.001% hydrophobic-CGRP, $\leq$1% cinnamon and/or ginger and/or peppermint oil, 1.0% L-Arginine, $\geq$9.990% vitamin E, $\geq$90% cocoa butter and/or DI water and/or polyglycerylmethacrylate and/or glycerine and/or carboxymethylcellulose and/or hydroxymethylcellulose and/or methylparaben and/or propylene glycol and/or polyethylene glycol and/or sodium benzoate.
12. 0.001% hydrophobic-CGRP, $\leq$1% cinnamon and/or ginger and/or peppermint oil, 1.0% L-Arginine, 1.0% L-Valine, $\geq$9.990% vitamin E, $\leq$90% cocoa butter and/or DI water and/or polyglycerylmethacrylate and/or glycerine and/or carboxymethylcellulose and/or hydroxymethylcellulose and/or methylparaben and/or propylene glycol and/or polyethylene glycol and/or sodium benzoate.
13. 0.001% hydrophobic-CGRP, $\geq$1% cinnamon and/or ginger and/or peppermint oil, 1.0% L-Arginine, 1.0% L-Valine, $\geq$9.990% vitamin E, $\leq$90% cocoa butter and/or DI water and/or polyglycerylmethacrylate and/or glycerine and/or carboxymethylcellulose and/or hydroxymethylcellulose and/or methylparaben and/or propylene glycol and/or polyethylene glycol and/or sodium benzoate.

14. 0.001% hydrophobic-CGRP, ≧1% cinnamon and/or ginger and/or peppermint oil, 1.0% L-Arginine, 1.0% L-Valine, ≧9.990% vitamin E, ≦90% cocoa butter and/or DI water and/or polyglycerylmethacrylate and/or glycerine and/or carboxymethylcellulose and/or hydroxymethylcellulose and/or methylparaben and/or propylene glycol and/or polyethylene glycol and/or sodium benzoate.

The foregoing description is considered as illustrative only of the principles of the invention. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. Furthermore, since a number of modifications and changes will readily occur to those skilled in the art, it is not desired to limit the invention to the exact construction and process shown described above. Accordingly, all suitable modifications and equivalents may be resorted to falling within the scope of the invention as defined by the claims which follow.

What is claimed is:

1. A method of treating Female Sexual Arousal Disorder by delivering a CGRP releasing substance selected from a member of the group consisting of hydrophobic-CGRP, said method comprising the step of topically administering to the clitoris a delivery vehicle for the substance, said delivery vehicle containing an effective amount of the substance sufficient to migrate from the delivery vehicle to the skin where the substance is absorbed by the surrounding tissue.

2. The method of claim 1, wherein said hydrophobic-CGRP is CGRP-linolenic acid.

3. The method of claim 1, wherein said hydrophobic-CGRP is Boc-[[(alaninyloxy)methyl]-carbonyl]-N-tryptophan benzyl ester.

4. The method of claim 1, wherein said delivery vehicle is selected from the group consisting of creams, gels, ointments, oils or sprays.

5. The method of claim 4, wherein said delivery vehicle is administered to the clitoris.

6. The method of claim 2, wherein the delivery vehicle comprising CGRP-linolenic acid in the range of 1–50 µg/dose is administered.

7. The method of claim 3, wherein the delivery vehicle comprising Boc-[[(alaninyloxy)methyl]-carbonyl]-N-tryptophan benzyl ester in the range of 1–50 µg/dose is administered.

8. The method of claim 1, wherein a delivery vehicle that is topically administered comprises CGRP-linolenic acid (0.0004–0.005%), L-Arginine (0–5%), L-Valine (0–5%), vitamin E (9–99.99%), cinnamon oil (0–≦5%), ginger oil (0–≦5%), peppermint oil (0–≦5%), *Gynostemma pentaphyllum* (0–≦10%) and *Crataegus pinnatifidia* (0–≦10%).

9. The method of claim 8, wherein the delivery vehicle is any combination of water, glycerine, cocoa butter, polyglycerylmethacrylate, methylparaben, carboxymethylcellulose, hydroxymethylcellulose, silicone, waxes, petroleum jelly, polyethylene glycol, propylene glycol, liposomes, transfersomes, vitamin E, or sugars.

10. The method of claim 8, wherein the delivery vehicle further comprises permeation enhancers.

11. The method of claim 10, wherein said permeation enhancers are selected from the group consisting of dimethylsulfoxide (DMSO), dimethyl formamide (DMF), N,N-dimethyl-acetamide (DMA), decylmethylsulfoxide (C10MSO), polyethylene glycol monolaurate (PEGML), glyceral monolaurate, lecithin, 1-substituted azacycloheptan-2-ones, L-Arginine, L-Valine, vitamin E, and 1-N-dodecylcyclazacylcoheptan-2-ones.

12. The method of claim 1, wherein a delivery vehicle that is topically administered comprises Boc-[[(alaninyloxy)methyl]-carbonyl]-N-tryptophan benzyl ester (0.0004–0.005%), L-Arginine (0–≦5%), L-Valine (0–≦5%), vitamin E (9–99.99%), cinnamon oil (0–≦5%), ginger oil (0–≦5%), peppermint oil (0–≦5%), *Gynostemma pentaphyllum* (0–≦10%) and *Crataegus pinnatifidia* (0–≦10%).

13. The method of claim 12, wherein the delivery vehicle is any combination of water, glycerine, cocoa butter, polyglycerylmethacrylate, methylparaben, carboxymethylcellulose, hydroxymethylcellulose, silicone, waxes, petroleum jelly, polyethylene glycol, propylene glycol, liposomes, transfersomes, vitamin E, or sugars.

14. The method of claim 12, wherein the delivery vehicle further comprises permeation enhancers.

15. The method of claim 14, wherein said permeation enhancers are selected from the group consisting of dimethylsulfoxide (DMSO), dimethyl formamide (DMF), N,N-dimethyl-acetamide (DMA), decylmethylsulfoxide (C10MSO), polyethylene glycol monolaurate (PEGML), glyceral monolaurate, lecithin, 1-substituted azacycloheptan-2-ones, L-Arginine, L-Valine, vitamin E, and 1-N-dodecylcyclazacylcoheptan-2-ones.

16. The method of claim 1, wherein said hydrophobic-CGRP is CGRP, CGRP analogues or polypeptides containing the active site of CGRP.

* * * * *